(12) United States Patent
Sommer et al.

US011000665B2

(10) Patent No.: US 11,000,665 B2
(45) Date of Patent: May 11, 2021

(54) FILTER AND DEVICE FOR ARTIFICIAL RESPIRATION HAVING A FILTER

(71) Applicant: WEINMANN EMERGENCY MEDICAL TECHNOLOGY GMBH + CO. KG, Hamburg (DE)

(72) Inventors: Andreas Sommer, Hamburg (DE); Matthias Pulla, Hamburg (DE); Stefan Hein, Hamburg (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 194 days.

(21) Appl. No.: 15/543,893

(22) PCT Filed: Jan. 8, 2016

(86) PCT No.: PCT/DE2016/000009
§ 371 (c)(1),
(2) Date: Jul. 14, 2017

(87) PCT Pub. No.: WO2016/131434
PCT Pub. Date: Aug. 25, 2016

(65) Prior Publication Data
US 2018/0326172 A1 Nov. 15, 2018

(30) Foreign Application Priority Data
Feb. 16, 2015 (DE) ..................... 10 2015 002 052.8

(51) Int. Cl.
*A61M 16/10* (2006.01)
*F24F 3/16* (2021.01)
(Continued)

(52) U.S. Cl.
CPC ...... *A61M 16/1055* (2013.01); *A61M 16/047* (2013.01); *A61M 16/107* (2014.02);
(Continued)

(58) Field of Classification Search
CPC ....... A62B 13/00; A62B 17/04; A62B 18/006; A62B 18/04; A62B 23/02; A62B 18/02;
(Continued)

(56) References Cited

U.S. PATENT DOCUMENTS 2,751,904 A * 6/1956 Lewis .................. A62B 18/025
128/206.17
2,796,143 A * 6/1957 Longenecker ......... A62B 13/00
312/244
(Continued)

FOREIGN PATENT DOCUMENTS

DE 102010047565 A1 4/2012
EP 0462412 A2 12/1991
(Continued)

*Primary Examiner* — Annette Dixon
(74) *Attorney, Agent, or Firm* — Lucas & Mercanti, LLP; Klaus P. Stoffel

(57) ABSTRACT

A hygiene filter for a device for artificial respiration, having at least one filter for filtering microorganisms and/or solid particles from a respiratory air volume flow, and a device for artificial respiration, having a holding device within the air intake region. The filter material is designed as a seal against the respiratory air volume flow conducting elements such that the risk of the occurrence of secondary air is reduced.

11 Claims, 12 Drawing Sheets

(51) Int. Cl.
*A61M 16/04* (2006.01)
*F24F 8/192* (2021.01)

(52) U.S. Cl.
CPC .............. *F24F 3/16* (2013.01); *F24F 8/192* (2021.01); *A61M 2205/125* (2013.01); *A61M 2205/7509* (2013.01); *A61M 2205/7518* (2013.01); *A61M 2205/7545* (2013.01)

(58) Field of Classification Search
CPC .............. A62B 18/025; B01D 2239/10; B01D 39/1623; B03C 3/28; D04H 13/00
See application file for complete search history.

(56) References Cited

U.S. PATENT DOCUMENTS

| | | | | |
|---|---|---|---|---|
| 4,069,026 A * | 1/1978 | Simm | ................ | B01D 39/1623 264/413 |
| 4,098,270 A * | 7/1978 | Dolby | .................... | A62B 18/02 128/206.12 |
| 4,677,976 A * | 7/1987 | Fujinuma | ............... | A62B 23/02 128/201.25 |
| 5,003,974 A * | 4/1991 | Mou | ..................... | A62B 17/04 128/201.25 |
| 6,554,881 B1 * | 4/2003 | Healey | ............... | B01D 39/1623 156/62.4 |
| 6,780,217 B1 | 8/2004 | Palmer | | |
| 6,858,057 B2 * | 2/2005 | Healey | ............... | B01D 39/1623 264/169 |
| 8,932,380 B2 * | 1/2015 | Okada | .................. | B01D 46/521 55/482 |
| 9,737,675 B2 * | 8/2017 | Frame | .................... | G16H 20/40 |
| 10,286,175 B2 * | 5/2019 | Holley | .................. | F01N 13/082 |
| 2003/0070406 A1 | 4/2003 | Duffy | | |
| 2013/0263854 A1 * | 10/2013 | Taylor | ................. | A61M 16/125 128/204.23 |

FOREIGN PATENT DOCUMENTS

| | | |
|---|---|---|
| EP | 1537903 A1 | 6/2005 |
| EP | 2572747 A1 | 3/2013 |
| WO | 2009149507 A1 | 12/2009 |

\* cited by examiner

FILTER AND DEVICE FOR ARTIFICIAL RESPIRATION HAVING A FILTER

The present application is a 371 of International application PCT/DE2016/000009, filed Jan. 8, 2016, which claims priority of DE 10 2015 002.052.8, filed Feb. 16, 2015, the priority of these applications is hereby claimed and these applications are incorporated herein by reference.

BACKGROUND OF THE INVENTION

The invention relates to a hygiene filter for a ventilation apparatus, having at least one filter for filtering microorganisms and/or solid particles from a breathing air volume flow.

Furthermore, the invention relates to a ventilation apparatus having a holding apparatus within the air intake region.

Filter devices are typically used in pneumatic devices in order to prevent particles from being drawn in. Frequently, blowers, fans or compressors are arranged downstream of the filter device in the direction of flow. A fine filter or coarse filter is typically arranged in the direction of flow in order to hold back relatively coarse impurities.

A bacteria-proof filter is fitted in the region of a hose line between a ventilator and a breathing mask of a patient in order to hold back impurities drawn in from the environment. In addition, such a filter in the hose line serves to prevent exhaled air that is possibly contaminated with bacteria from being breathed back into the ventilator. A disadvantage of known solutions is that bacteria and viruses can pass from the ambient air into the ventilator through the intake region. Such a contaminated device has to be hygienically treated laboriously. They protect at least the patient from contamination, but not the ventilator.

Upon implementation in connection with medical devices, it is possible, however, for health impairments to arise in patients who use the devices in question when germs or viruses pass from the ambient air or from the ventilation apparatus into the patient's airways by ventilation. Respiratory infections (tuberculosis, tracheobronchitis or pneumonia) represent the largest group of infections that occur in hospitals, intensive care units and the emergency services. The transnational spread of infectious diseases, known as pandemics, are becoming increasingly significant and are gaining more and more attention, since they can spread very rapidly via our current rapid transport systems, including air tourism. This effect also became apparent in the spread of SARS in 2003. The most recent example that may also be mentioned is the influenza infection known as swine flu.

Germs can be transmitted via contaminated ventilators. The devices are in this case contaminated with germs for example by the patient breathing back into the device, or, in what is known as the air-mix mode (in which ambient air is drawn in), by germs which are located in the ambient air and are drawn in by the device. Depending on type, contaminated devices have to be hygienically treated laboriously or replaced.

In order to avoid transmission of germs between patients and to save on expensive hygienic treatment of the device, an exchangeable, bacteria- and virus-proof filter for the air intake region of a ventilation apparatus is used, said filter also having a filter change display which specifies the change intervals to the user. Devices with filter systems for viruses and bacteria help to save costs in the healthcare sector and—by protection from contamination—to increase patient safety.

The aim of avoiding transmission of germs between patients without hygienically treating the devices used can be achieved through the use of exchangeable, bacteria- and virus-proof filters for the air intake region of a ventilation apparatus, if it is ensured both that the undesired bacteria and viruses are retained reliably by the filter material used and that the microorganisms are not provided with any other way of passing through the filter.

SUMMARY OF THE INVENTION

The object of the present invention is to provide a filter material that is suitable for microorganisms such as bacteria and viruses and also solid particles of various sizes, and the structural design thereof, said filter material being usable in a ventilation apparatus of the type mentioned in the introduction and being designed such that microorganisms and/or solid particles are substantially separated from the volume flow passing through the filter.

This object is achieved according to the invention in that a bacteria-, virus- and/or particle-proof filter material in combination with a filter holder coordinated with the filter material is configured in an exchangeable manner and such that organisms and/or particles substantially cannot pass through the filtering location within the air intake region of a ventilation apparatus, and so a low-contamination space downstream of the filtering location in the direction of flow is supported.

The teaching according to the invention recognizes that the situation of a low-contamination space downstream of the filtering location in the direction of flow is supported in particular when the filter material has the requisite filtering properties and/or no parts of the volume flow flow past the filter material and thus remain unfiltered and/or the filter or the filter material is arranged so as to be exchangeable after a degree of soiling that is unfavorable for the filtering properties has been reached.

In one variant embodiment, according to the invention, a filter holder for a bacteria- and virus-proof filter material is mounted in the air intake region of a device housing and is arranged so as to be exchangeable relative thereto.

As a result of an at least partially asymmetrical formation of the filter holder and the at least temporary connection of filter and filter frame to a hygiene filter system, it is not possible to fix the hygiene filter system in the wrong position in the region of the device housing.

Tilt-proof mounting is allowed in that the device housing provides, in the region of the receptacle for the hygiene filter system, a bearing surface for the hygiene filter system.

In order to help securely fix the hygiene filter system in an intended operating state, a latching element for fixing the hygiene filter system in the region of the device housing is arranged substantially opposite the support.

Easy manual handling is supported in that the latching element is formed at least regionally in a resiliently deformable manner.

Good accessibility for a filter change is achieved in that the filter holder forms at least regionally as a pivoting holder.

Depending on the filter material used, it is possible according to the invention for the hygiene filter system to be formed, without a frame, filter housing or the like, only from the filter material, which is fixable in the filter holder in a ventilation apparatus of the type mentioned in the introduction. In this exemplary embodiment, the filter material, in addition to the required filter property and mechanical-structural strength, also has to be suitable to provide reliable sealing with respect to the filter holder, in order to avoid secondary air.

In a preferred application, the device housing is formed as part of an emergency ventilator.

High functionality with at the same time high mechanical stability is achieved in one of the possible variant embodiments in that the filter holder is formed in a foldable manner and has recesses and at least one edging web for the filter.

A good filter effect with simultaneously low flow resistance is achieved in that the filter is electrostatically charged.

The ventilator with a hygiene filter system is distinguished by the following properties and functions:
- protection of the entire device from bacteria and viruses and/or particles
- filter change is selectively possible with or without a tool by the user
- operation with a dirty filter has to be impossible
- filter change interval is specified by the device, depending on the operating period The following specifications of the hygiene filter system can be achieved according to a variant of the invention:
- degree of separation of 99.99% at a particle size of 0.027 μm
- filter size of about 10 cm² at a maximum flow rate of 60 l/min
- resistance at 60 l/min at most 5 cm $H_2O$ Modifications can be made for other filter sizes.

The hygiene filter is fitted in a filter flap and sealed off there, in order to prevent unfiltered secondary air from passing into the ventilator.

The degree of soiling of the hygiene filter is determined via resistance measurement and/or an operating hours counter which is always set to zero when a new filter is fitted. A sensor for sensing the filter resistance determines the through-flow. The through-flow is evaluated over time in order to detect decreasing flow. From a definable limit value, the filter change display is activated.

Hydrophobic filters are impermeable to liquids. The use of small fiber spacings and the use of liquid-repellent fibers bring about the hydrophobic properties. As a result, in these filters, there is no restriction of the filter performance and no increase in resistance in a damp environment. Hydrophobic filters hold back particles starting at 20 nanometers (nm). Thus, even viruses, which typically have a size of between 20 and 300 nm, are held back. Bacteria and the spores thereof have a typical size in the range of 500 nm to 2000 nm and are thus reliably held back by hydrophobic filters.

In electrostatic filters, the filter medium is negatively and positively charged. The pore width is greater than in hydrophobic filters, for which reason there is a lower resistance at the same through-flow rate. Bacteria or viruses contained in the air stream are attracted and thus held back by the charged filter material on account of their surface charge and regardless of their size.

According to the invention, the use of a combination of both filter types is also provided.

One solution approach is a coarse-pored filter material, which has an electrostatic charge in order to filter bacteria and viruses.

The hygiene filter material according to the invention can have a high through-flow rate of up to 60 l/min over an area of less than 20 cm² with at the same time a virtually absolute filter performance (99.9%) with respect to viruses and bacteria.

In addition, the resistance of the filter is scarcely influenced by moisture. The resistance does not exceed a value of 5 cm $H_2O$ at a flow of 60 l/s.

For the device input filter, i.e. a filter apparatus for the air intake region of a ventilation apparatus, very good sealing has to be achieved at the interfaces with the device. Secondary air, i.e. parts of the volume flow that do not pass through the filter, absolutely has to be avoided in order to ensure low-germ breathing gas, i.e. breathing gas with as few viruses, bacteria and/or solid particles as possible. In addition, the handling and operability of the filter system in the event of maintenance have to be designed to be as easy and robust as possible. Clear, distinctive mechanical interfaces and a favorable material choice should ensure positioning accuracy. Positioning accuracy is responsible, inter alia, for the fact that the entire volume flow without secondary air flows through the filter.

The present invention is suitable for emergency ventilators, home ventilators or hospital ventilators and also for inhalation devices and oxygen devices.

Exemplary embodiments of the invention are schematically illustrated in the drawings, in which:

DETAILED DESCRIPTION OF THE INVENTION

Figure 1:
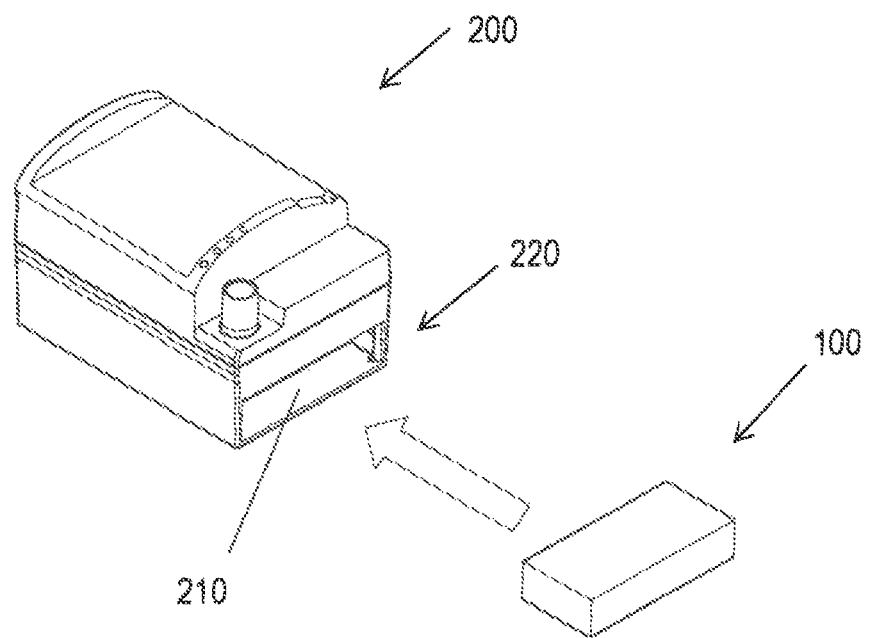
FIG. 1 shows a perspective view of a ventilation apparatus having a hygiene filter system.

FIG. 1 depicts a perspective view of a ventilation apparatus (200) with a hygiene filter system (100) In the exemplary embodiment shown in FIG. 1, the hygiene filter system (100) can be fitted into a holding apparatus (210) within the air intake region (220) of a ventilation apparatus (200).

Figure 2:
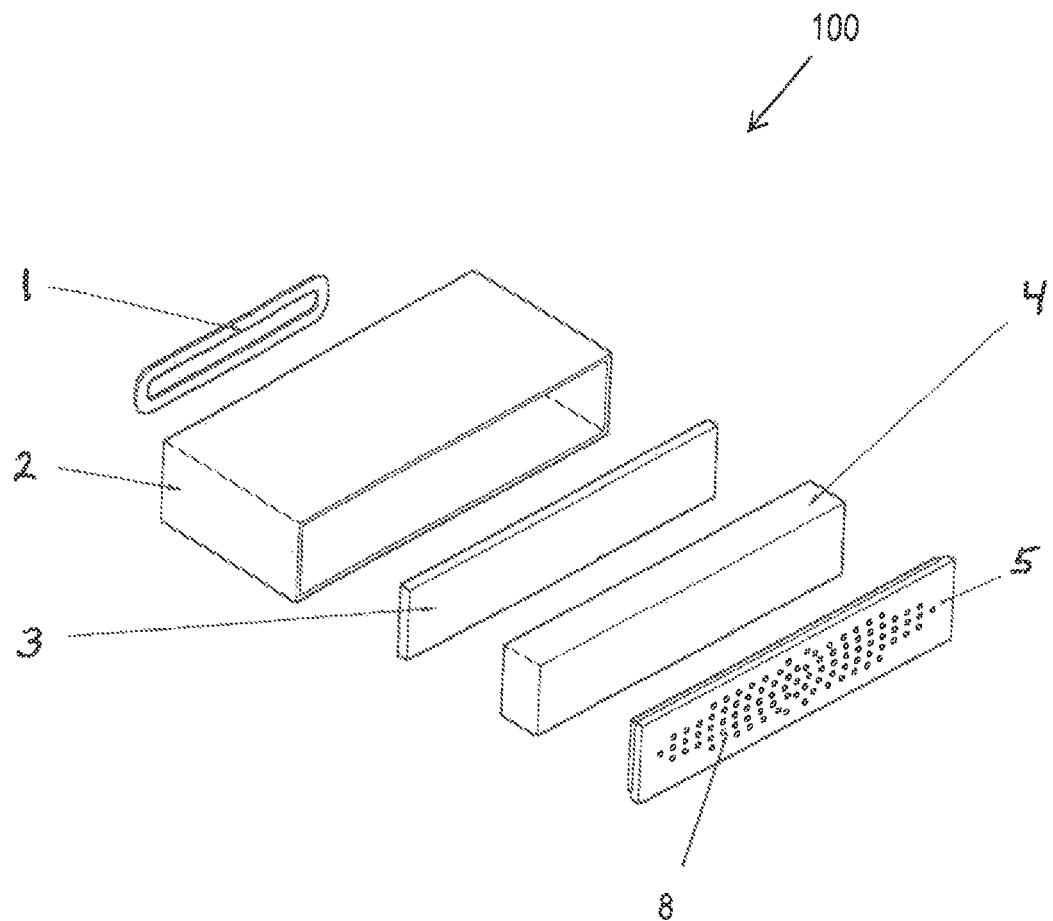
FIG. 2 shows an exploded illustration of a first exemplary embodiment of a hygiene filter system.

FIG. 2 shows a perspective exploded illustration of a first exemplary embodiment of the hygiene filter system (100) according to the invention. In this first exemplary embodiment, the hygiene filter system (100) is arranged within a housing (2) and also consists substantially of at least one fine filter (3) and at least one coarse filter (4) arranged upstream of the fine filter (3) in the direction of volume flow.

The intake cover (5) closes the housing (2) off from the environment and is configured such that first coarsest impurities in the ambient air to be drawn in are held back—realized here, for example, by a multiplicity of intake bores (8) with a suitable diameter smaller than the coarsest impurities to be held back. Provided on the housing (2) of the hygiene filter system (100) and arranged in the installation direction with respect to the ventilation apparatus (200) is a housing opening (9) (not illustrated in FIG. 2) with a seal (1).

Preferably, the housing opening (9) is positioned opposite the intake cover (5).

Depending on the selected material, the housing parts can be snapped together, welded or adhesively bonded. Preferably, the intake cover (5) is connected releasably to the housing (2), in order to support the filter change or the cleaning thereof on account of the resultant accessibility.

Figure 3:
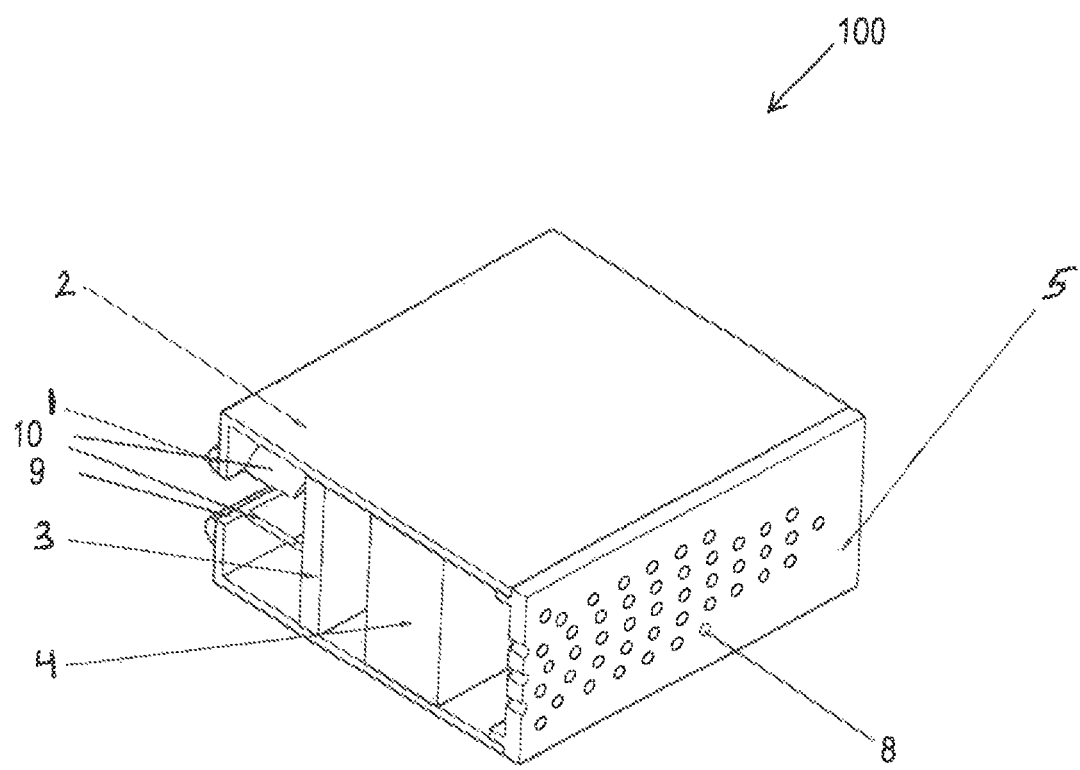
FIG. 3 shows a perspective sectional illustration of a first exemplary embodiment of a hygiene filter system.

FIG. 3 shows a three-dimensional sectional illustration of the first exemplary embodiment of the hygiene filter system (100), with the preferred arrangement of the coarse filter (4) and fine filter (3) one after the other as seen in the direction of volume flow. Ambient air is drawn in through the intake bores (8) in the intake cover (5). In order to effectively prevent secondary air, the housing (2) is equipped with a seal (1) at its interface formed by a housing opening (9) in the direction of the ventilation apparatus (200). In order to improve the stability of the housing (2), in particular at the interface in the direction of the ventilation apparatus (200), ribs (10) can be provided as stiffening webs. As a result, deformation of the sealing surfaces, which can be the cause of leaks and thus secondary air, is reduced. In a preferred configuration of the seal (1), the latter is produced from silicone or on the basis of silicone.

The first exemplary embodiment of the hygiene filter system (100) according to the invention is configured such that the position of the housing opening (9) is provided off-center on the end side of the housing contour. As a result of the off-center position, the hygiene filter system (100) can be fitted only in one desired position and orientation in the holding apparatus (210) of the ventilation apparatus (200)—in this way, the handling and operability of the filter system in the event of maintenance are as easy and robust as possible and provide a clear and defined distinctive mechanical interface. In this way, installation in the wrong position is ruled out and operation without secondary air is supported.

According to another variant embodiment, the hygiene filter system (100) is formed in a symmetrical manner and can be installed in both positions.

Figure 4:
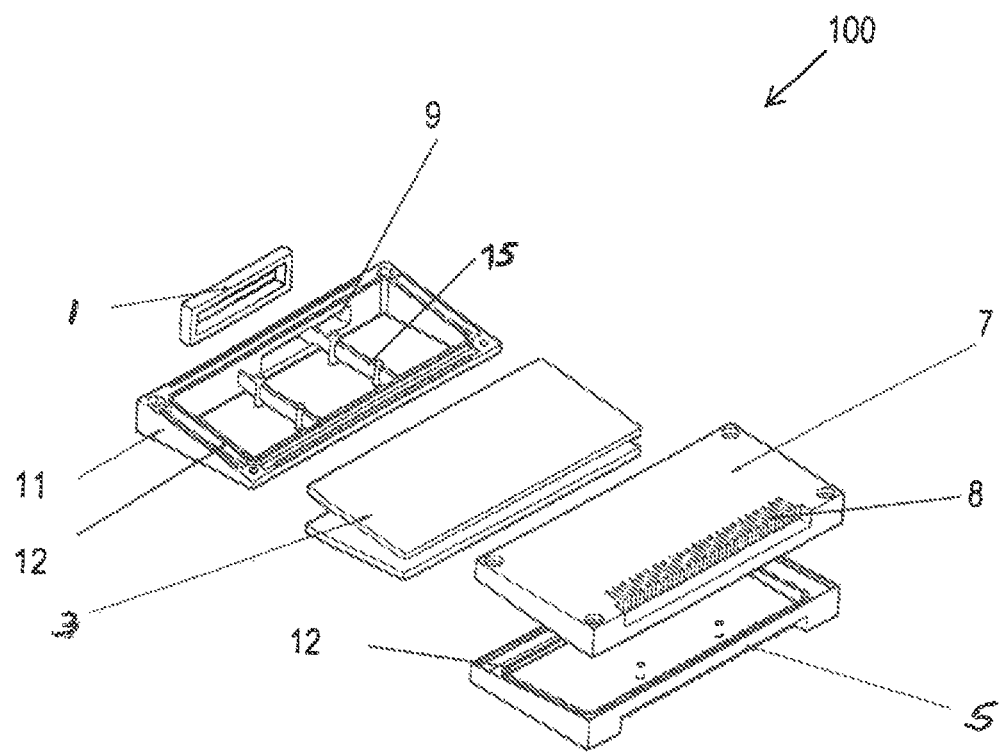
FIG. 4 shows a perspective exploded illustration of a second exemplary embodiment of a hygiene filter system.

FIG. 4 depicts a perspective exploded illustration of the second exemplary embodiment of the hygiene filter system (100). Unlike the first exemplary embodiment according to FIGS. 2 and 3, the housing is split in the longitudinal direction and formed from at least one intake cover (5), a filter cover (7) and a filter material holder (11). The fine filter (3) in the second exemplary embodiment is formed by fleece material and, in a preferred configuration, can have electrostatic properties. The fine filter (3) is configured in a sheet-like manner and arranged in a wedge-shaped manner within the housing (5, 7). The fine filter (3) is fixed in and relative to the housing by being clamped between the filter material holder (11) and in each case the intake cover (5) and the filter cover (7), respectively.

The filter material holder (11) can be internally equipped with at least one spacer (15) for example in the form of a rib in order to increase the mechanical stability of the frame-like filter material holder (11) and to keep the preferably electrostatic fine filter (3) in the desired plane and to prevent sagging into the filter material holder (11).

As a result of the wedge-shaped arrangement of the fine filter (3) within the hygiene filter system (100) rather than the right-angled orientation in the housing, the useful filter surface area is not limited by the housing cross section at this point and can be larger in the scope of the known mathematical trigonometric relationships.

The second exemplary embodiment of the hygiene filter system (100) according to the invention, too, is configured such that the position of the housing opening (9) is provided off-center on the end side of the housing contour in order to support the installation of the hygiene filter system (100) only in one desired position and orientation in the holding apparatus (210) of the ventilation apparatus (200).

Figure 5:
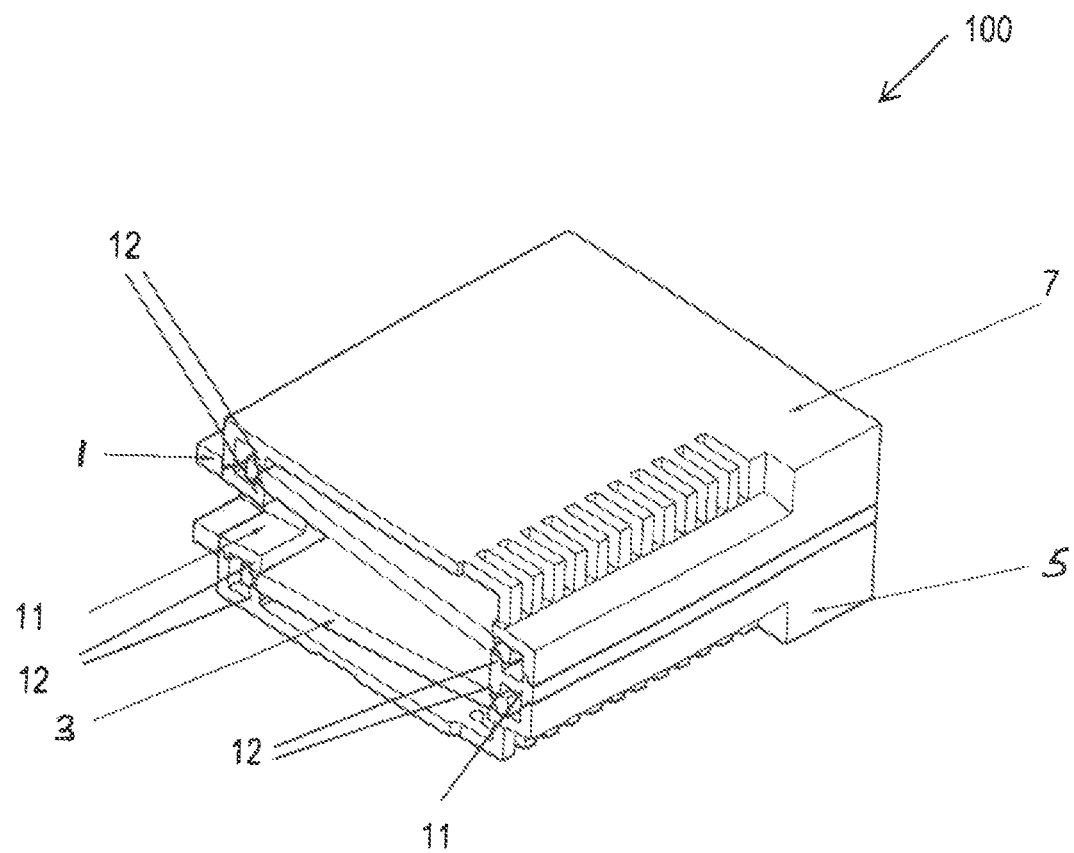
FIG. 5 shows a three-dimensional sectional illustration of a second exemplary embodiment of a hygiene filter system.

FIG. 5 shows a three-dimensional sectional illustration of the second exemplary embodiment of the hygiene filter system (100) with the wedge-shaped arrangement of the fine filter (3) within the hygiene filter system (100) rather than the right-angled orientation in the housing, and the resultant useful filter surface area that is much larger, i.e. by up to a factor of about four to five, compared with the housing cross section. As a result, the filter surface can be about 10.000 $mm^2$ when the clear cross section of the housing is 2000 to 2500 $mm^2$.

The elements (5, 7, 11) that form the housing are preferably connected together by being snapped together. In order to ensure reliable clamping of the fine filter (3), the housing-forming elements (5, 7, 11) can additionally or optionally have webs (12) in the form of housing edges. This ensures that the risk of secondary air is reduced. The webs (12) can be arranged such that the fine filter (3) is clamped on one side or on both sides.

Figure 6:
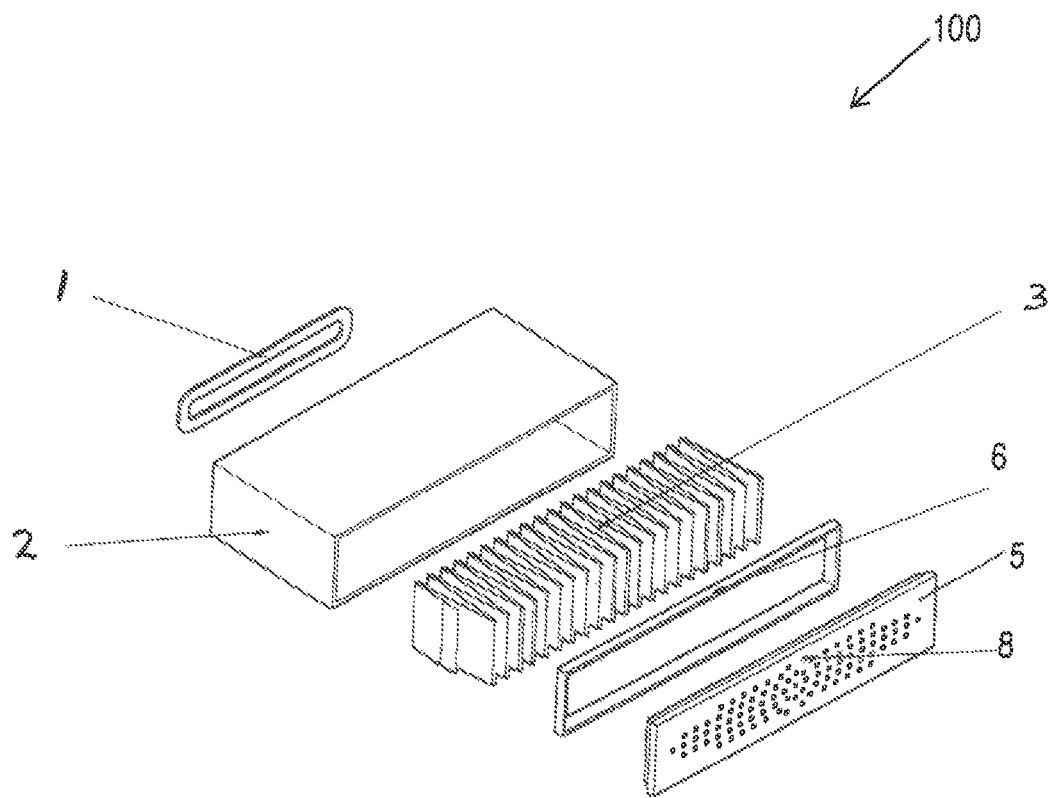
FIG. 6 shows a perspective exploded illustration of a third exemplary embodiment of a hygiene filter system.

FIG. 6 depicts a perspective exploded illustration of a third exemplary embodiment according to the invention of the hygiene filter system (100). The structure of the housing (2) is similar to the first exemplary embodiment illustrated in FIGS. 2 and 3. In contrast thereto, the filter material is folded and the folded layers are arranged in a manner spaced apart from one another such that the surface of the filter material also provides an active surface for the filtering process between the folded layers.

The folded fine filter (3) can, in this way, have a useful filter surface area that is increased by up to a factor of about seven compared with the construction according to exemplary embodiment two and a useful filter surface area that is increased by up to a factor of about 35 compared with the construction according to exemplary embodiment one. As a result, the filter surface can be approximately 70.000 $mm^2$ when the clear cross section of the housing is 2000 to 2500 $mm^2$.

The folded fine filter (3) is oriented within the housing such that the volume flow of the medium to be filtered flows in radially at the respective folded edges.

The housing parts can be welded or adhesively bonded, depending on the selected material. Preferably, the folded fine filter (3) is fixed within the housing (2) and sealed off by a casting compound (6) such that secondary air is largely prevented. In the case of the hygiene filter system (100) according to the third exemplary embodiment, provision is therefore not generally made for a filter material change.

Figure 7:
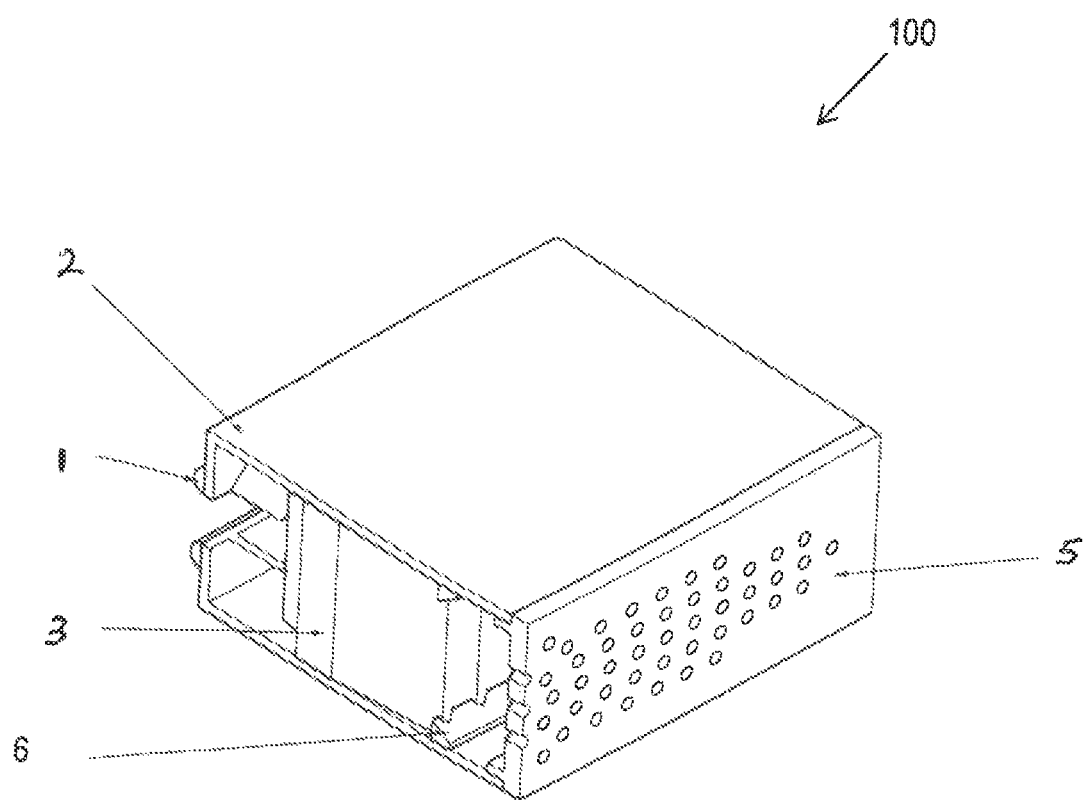
FIG. 7 shows a perspective sectional illustration of a third exemplary embodiment of a hygiene filter system.

FIG. 7 shows the situation according to FIG. 6 as a three-dimensional sectional illustration.

Figure 8:
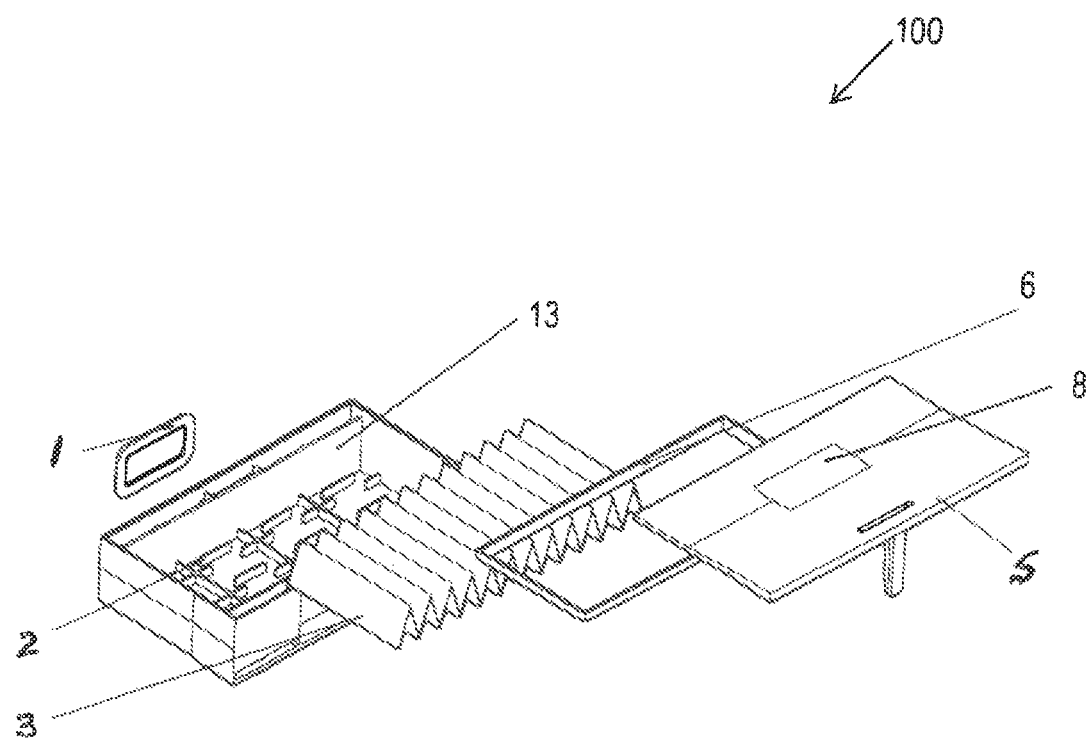
FIG. 8 shows a perspective exploded illustration of a fourth exemplary embodiment of a hygiene filter system.

FIG. 8 depicts a perspective exploded illustration of a fourth exemplary embodiment according to the invention of the hygiene filter system (100).

Use is made of a folded fine filter (3), which is fixed with its folded edges parallel to the longitudinal orientation of the hygiene filter system (100) within the housing (2) and sealed off with respect to undesired secondary air by casting compound. (6).

In the fourth exemplary embodiment, too, the folded fine filter (3) is oriented within the housing such that the volume flow of the medium to be filtered flows in radially at the respective folded edges.

In order to realize this radial incident flow at the filter edges by the volume flow of the medium to be filtered, two different possibilities are provided: if an intake cover (5) on the end side and opposite the housing opening (9) is used, the volume flow is guided by suitable internal housing walls (13) and in a suitable manner in a double S shape.

If—as illustrated—an intake cover (5) is used on the top side and opposite the housing opening (9), the medium to be filtered flows into the hygiene filter system (100) at an angle to the housing opening (9) via the intake opening (8) in the intake cover (5) and flows radially against the filter edges. In this case, the volume flow is guided by suitable internal housing walls (13) and in a suitable manner in an S shape.

Figure 9:
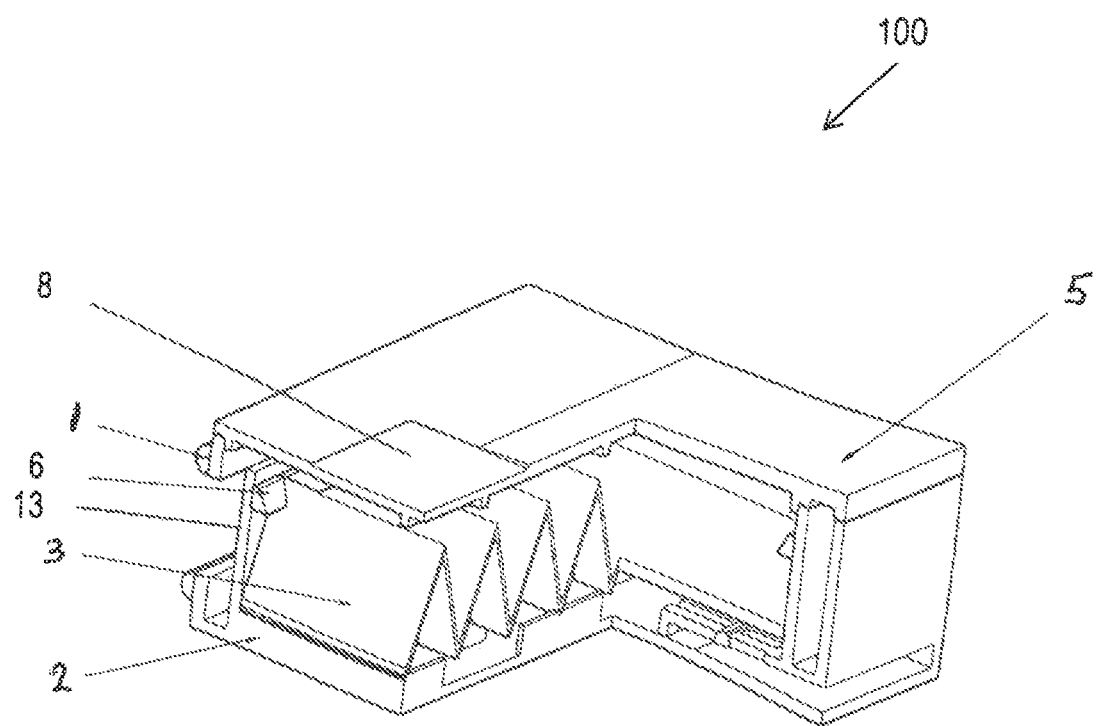
FIG. 9 shows a perspective sectional illustration of a fourth exemplary embodiment of a hygiene filter system.

FIG. 9 shows the situation according to FIG. 8 as a three-dimensional sectional illustration.

Figure 10:
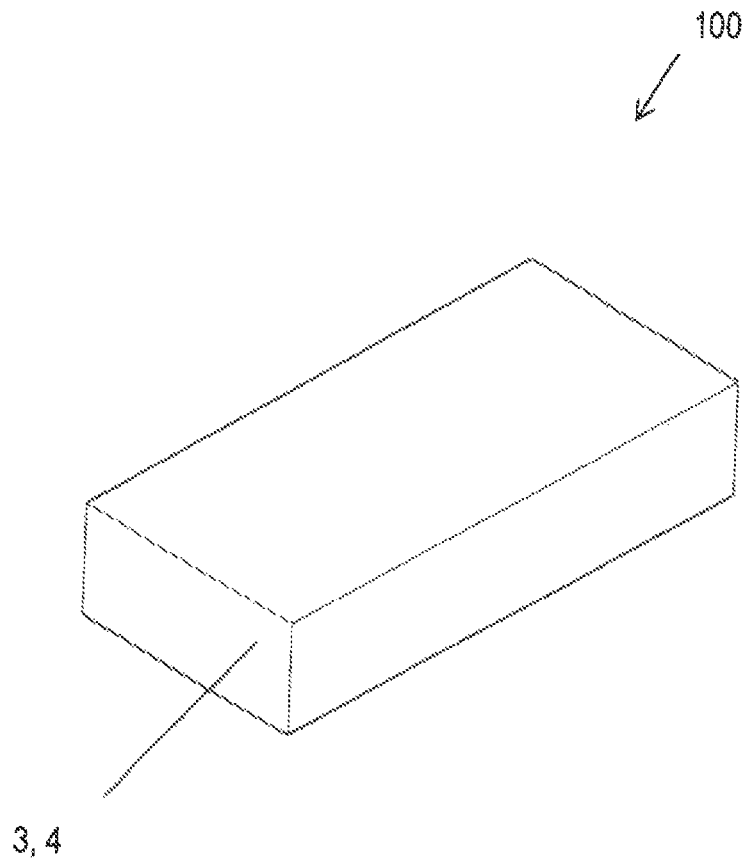
FIG. 10 shows a perspective illustration of a fifth exemplary embodiment of a hygiene filter system.
Figure 11:
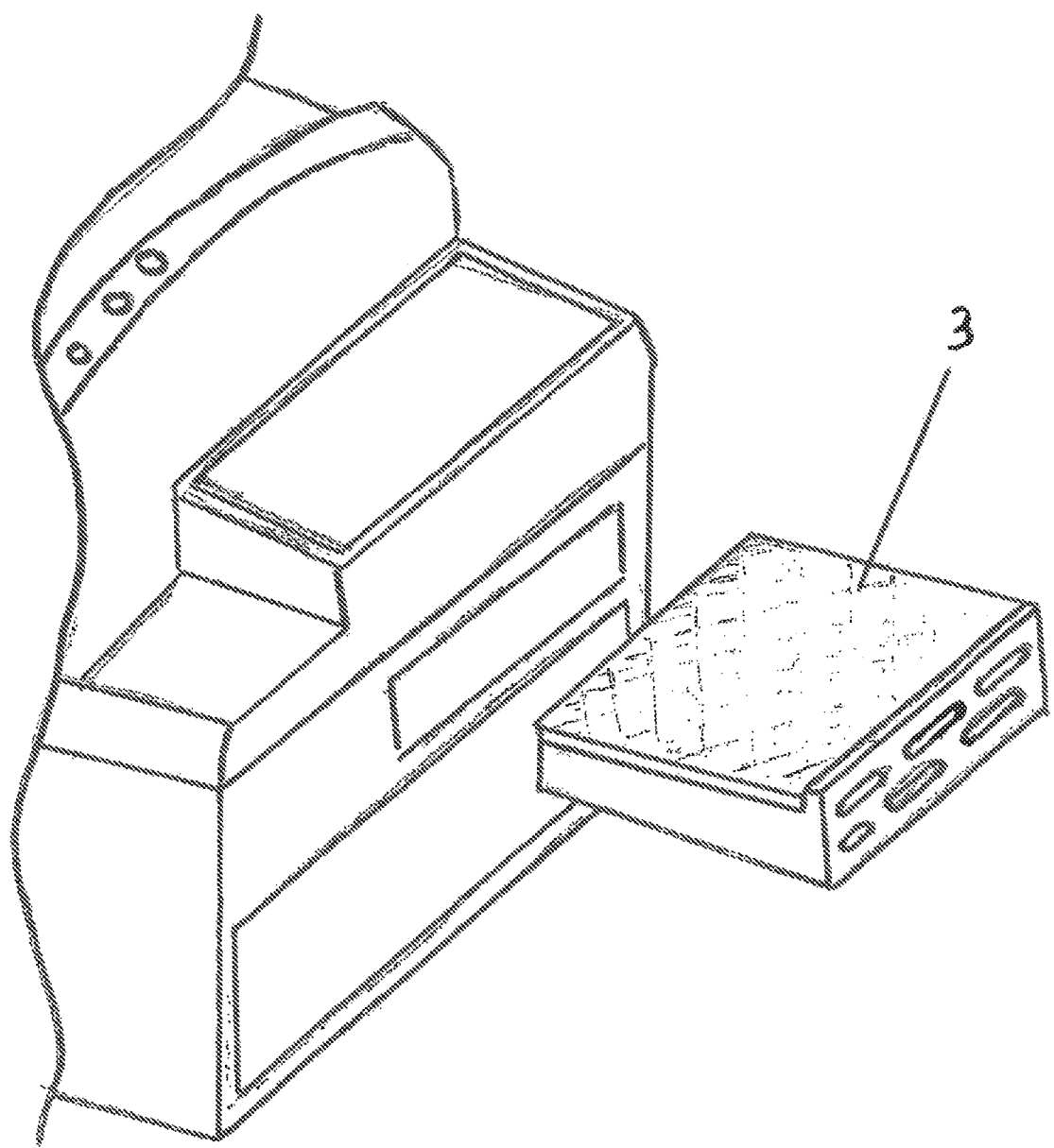
FIG. 11 shows a variant embodiment in which a seal is provided by the filter.
Figure 12:
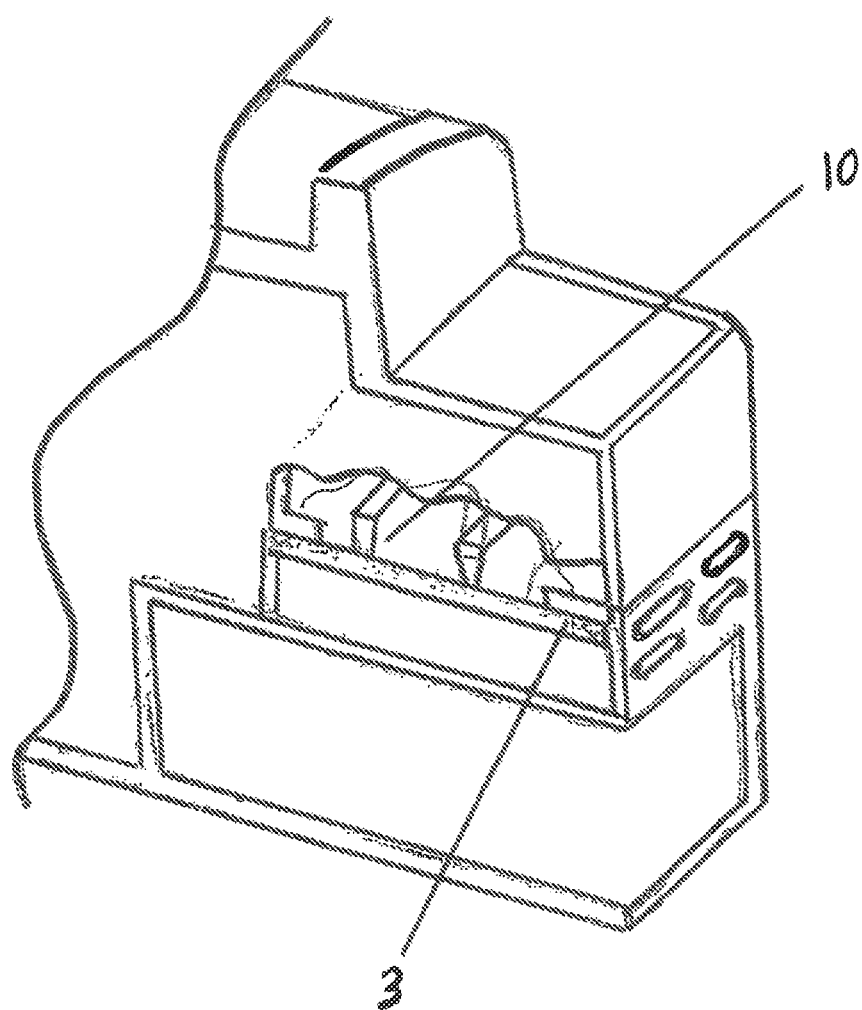
FIG. 12 shows an embodiment similar to FIG. 11, in which guiding ribs are used which keep the filter in a predefinable position.

FIG. 10 shows a perspective illustration of a fifth exemplary embodiment of the hygiene filter system (100). In this exemplary embodiment, the hygiene filter system (100) is realized without a housing (2) and consists substantially of at least one suitable filter material which, in order to be able to be used as a compatible alternative to the preceding exemplary embodiments in the holding apparatus (210) for a hygiene filter system (100) of a ventilation apparatus (200), in the case of nonelastic filter material properties, the external dimensions of the filter (3, 4) have to correspond substantially to those of the housing dimensions of the preceding exemplary embodiments, or, in the case of elastic filter material properties, the filter can have larger external dimensions. The filter material can consist of one or more materials.

For the problem of undesired secondary air, it is particularly advantageous for the filter (3, 4) to have elastic filter material properties, to be formed with an oversize with respect to the housing dimensions and for the filter material to have sealing properties. On account of the resulting at least partially elastic or elastic-plastic compression of the filter (3, 4) as a result of the reduction in the dimensions of the hygiene filter system (100) upon fitting in the holding apparatus (210) for a hygiene filter system (100) of a ventilation apparatus (200), the filter material presses in a sealing manner against the holding apparatus (210) and reduces the risk of secondary air.

Depending on the conditioning of a material or arrangement of several materials, there can be completely or partially different filter properties, which result in the filtering of different particles or microorganisms. For example, a foam mattress having a homogeneous or inhomogeneous structure can be used, such that the filter effect is completely or regionally different. Different material conditionings can be for example electrostatic and/or antibacterial properties.

When the seal with respect to the device is produced from an electrostatic filter material, it is also possible to support sufficient freedom from germs even in the event of a slight leak. Given a corresponding electrostatic charge, viruses and/or bacteria are attracted electrostatically by the filter material. Additional design variants consist in the provision of a wedge shape and/or the use of air-guiding ribs.

Given a corresponding wedge-shaped design, the filter material is pressed against the sealing surface by a wedge-shaped design of the housing.

We claim:

1. A ventilation apparatus with a hygiene filter, comprising: a hygiene filter system that includes at least one filter material for filtering microorganisms and/or solid particles from a breathing air volume flow, wherein the filter material is configured as a seal with respect to elements that guide the breathing air volume flow so that a risk of secondary air occurring is reduced;

and a housing that arranges the filter material and forms an element that guides the breathing air volume flow, wherein the housing is configured so as to be insertable into an inner area of a holding apparatus of the ventilation apparatus, wherein the housing is wedge-shaped so that the filter material is pressed against a sealing surface to form a wedge-shape, wherein the sealing surface is an inside surface of the holding apparatus, wherein the filter material seals the sealing surface of the holding apparatus against the housing, and wherein the filter material includes a fine filter and a coarse filter arranged so that the volume flow first passes through the coarse filter and subsequently through the fine filter, wherein the filter material has elastic properties and wherein a combination of the filter material and the housing is insertable in the inner area of the holding apparatus so that the wedge-shaped filter material is pressed against the wedge-shaped sealing surface, wherein the filter material provides a seal, wherein the filter material is formed plate-like, and wherein the filter material is arranged to support a flow direction of the breathing air that runs at least in part perpendicular to the plate-like filter material.

2. The ventilation apparatus according to claim 1, wherein the at least one filter material has homogeneous or partially different mechanical properties and filter effects.

3. The ventilation apparatus according to claim 1, wherein the filter material is a foam mattress or an electrostatic filter fleece.

4. The ventilation apparatus according to claim 1, wherein the filter material is folded.

5. The ventilation apparatus according to claim 1, further comprising a casting compound that seals off the filter material from the housing, in addition to the sealing by the filter material.

6. The ventilation apparatus according to claim 1, wherein the housing has internal walls arranged to guide breathing air volume flow in a double S-shaped or S-shaped manner within the housing.

7. The ventilation apparatus according to claim 1, wherein the housing has at least one housing opening arranged off-center on an end side of a housing contour, so that the hygiene filter system is insertable into the holding apparatus of the ventilation apparatus in only one position and orientation.

8. The ventilation apparatus according to claim 1, wherein the housing has at least one rib arranged to stiffen the housing.

9. The ventilation apparatus according to claim 8, wherein the at least one rib is additionally configured as a spacer.

10. The ventilation apparatus according to claim 1, wherein the hygiene filter is sealed off via at least a part of the holding apparatus.

11. The ventilation apparatus according to claim 10, further comprising an electrostatic filter material that seals off the hygiene filter system.

\* \* \* \* \*